(12) United States Patent
Westphal

(10) Patent No.: US 9,007,579 B2
(45) Date of Patent: Apr. 14, 2015

(54) DEVICE AND METHOD FOR MEASURING LUMINESCENCE

(75) Inventor: Peter Westphal, Jena (DE)

(73) Assignee: Carl Zeiss Microscopy GmbH (DE)

( * ) Notice: Subject to any disclaimer, the term of this patent is extended or adjusted under 35 U.S.C. 154(b) by 763 days.

(21) Appl. No.: 12/937,474

(22) PCT Filed: Apr. 4, 2009

(86) PCT No.: PCT/EP2009/002495
§ 371 (c)(1),
(2), (4) Date: Nov. 10, 2010

(87) PCT Pub. No.: WO2009/124698
PCT Pub. Date: Oct. 15, 2009

(65) Prior Publication Data
US 2011/0122402 A1    May 26, 2011

(30) Foreign Application Priority Data
Apr. 11, 2008  (DE) .......................... 10 2008 018 475

(51) Int. Cl.
  *G01N 21/64* (2006.01)
  *G01J 1/30* (2006.01)
  *G02B 21/00* (2006.01)
(52) U.S. Cl.
  CPC ........ *G01N 21/6408* (2013.01); *G01N 21/6458* (2013.01); *G02B 21/0076* (2013.01)
(58) Field of Classification Search
  USPC .................... 356/317–319, 326, 417, 217; 250/458.1, 459.1, 461.2
  See application file for complete search history.

(56) References Cited

U.S. PATENT DOCUMENTS 4,055,768 A  * 10/1977 Bromberg .................. 250/461.2
4,437,772 A  * 3/1984 Samulski ...................... 374/129
(Continued)

FOREIGN PATENT DOCUMENTS

DE       151222      10/1981
DE       3518527      5/1985
(Continued)

OTHER PUBLICATIONS

"Tau mapping of the autofluorescence of the human ocular fundus", Schweitzer et al., Proc. SPIE vol. 4164, p. 79-89, Laser Microscopy, Karsten Koenig; Hans J. Tanke; Kerbert Schneckenburger; Eds. (in paragraph [0058]).

*Primary Examiner* — Sang Nguyen
(74) *Attorney, Agent, or Firm* — Mayback & Hoffman, P.A.; Gregory L. Mayback; Rebecca A. Tie

(57) ABSTRACT

An optical device for measuring luminescence includes a pulse generator for generating a periodic modulation signal having rectangular pulses, a pulse duration of the pulse being variably adjustable, an illumination device and/or means for illuminating an object under investigation with excitation radiation modulated in a pulse-like manner depending on the modulation signal, and a time-of-flight camera for phase-sensitive detection of a luminescence response emitted by the object under investigation in response to the excitation radiation. The modulation signal is supplied as reference signal to the time-of-flight camera. A method of measuring luminescence includes generating the periodic modulation signal having rectangular pulses, generating the signal-dependent, pulse-modulated excitation radiation, illuminating the object with the radiation, providing the modulation signal as reference signal to the camera, and performing phase-sensitive detection with the camera of the luminescence response emitted by the object in response to the excitation radiation for different pulse durations.

28 Claims, 7 Drawing Sheets

(56) References Cited

U.S. PATENT DOCUMENTS

| | | | |
|---|---|---|---|
| 5,504,337 A * | 4/1996 | Lakowicz et al. | 250/461.2 |
| 5,548,124 A * | 8/1996 | Takeshima et al. | 250/458.1 |
| 5,784,162 A * | 7/1998 | Cabib et al. | 356/456 |
| 6,603,546 B1 * | 8/2003 | Barbieri et al. | 356/318 |
| 6,741,346 B1 * | 5/2004 | Gerstner et al. | 356/318 |
| 6,816,256 B1 * | 11/2004 | Lloyd | 356/317 |
| 6,965,431 B2 * | 11/2005 | Vo-Dinh et al. | 356/301 |
| 6,999,166 B2 * | 2/2006 | Matsushita et al. | 356/317 |
| 7,154,661 B2 * | 12/2006 | Seah et al. | 359/326 |
| 7,781,221 B2 * | 8/2010 | Mueller | 436/127 |
| 2004/0051051 A1 * | 3/2004 | Kato et al. | 250/458.1 |
| 2005/0075575 A1 * | 4/2005 | Vo-Dinh | 600/476 |
| 2007/0096039 A1 * | 5/2007 | Kapoor et al. | 250/458.1 |
| 2009/0040518 A1 * | 2/2009 | Widengren | 356/317 |
| 2009/0121154 A1 * | 5/2009 | Westphal et al. | 250/484.4 |

FOREIGN PATENT DOCUMENTS

| | | |
|---|---|---|
| DE | 69331629 | 3/1993 |
| DE | 4429383 | 8/1994 |
| DE | 19718016 | 4/1997 |
| DE | 19829657 | 8/1997 |
| DE | 19857792 | 12/1998 |
| DE | 19920158 | 4/1999 |
| DE | 10038080 | 8/2000 |
| DE | 102004006960 | 2/2004 |
| EP | 1162827 | 3/2003 |
| GB | 2126717 | 8/1983 |
| WO | 0138856 | 5/2001 |
| WO | 2004065944 | 8/2004 |
| WO | 2006130105 | 12/2006 |

* cited by examiner

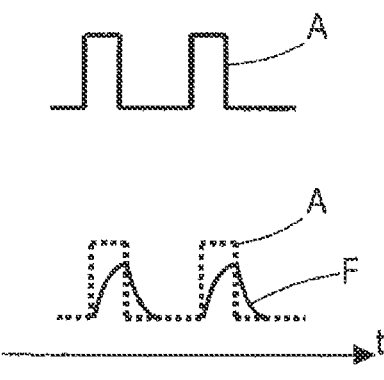
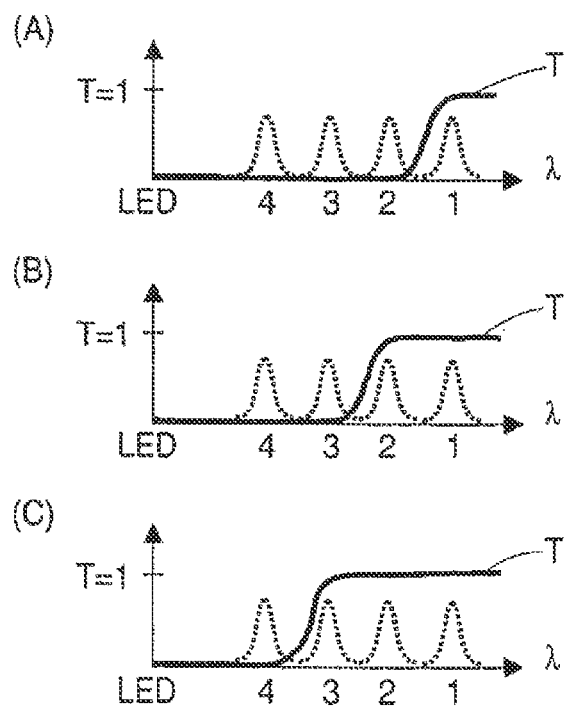
Fig.3
Fig.4

DEVICE AND METHOD FOR MEASURING LUMINESCENCE

CROSS-REFERENCE TO RELATED APPLICATIONS

This application claims the priority, under 35 U.S.C. §119, 120, 363, and 371, of German patent application No. 10 2008 018 475.6, filed Apr. 11, 2008, and International Application No. PCT/EP2009/002495, filed Apr. 4, 2009, which designated the United States and was not published in English; the prior applications are herewith incorporated by reference in their entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

SEQUENCE LISTING

Not Applicable

BACKGROUND OF THE INVENTION

In analysis methods using microscope-like arrangements it is known to analyze the luminescence lifetime, in particular the fluorescence lifetime, of certain materials, so-called fluorophores, so as to gain information on the analyzed object, e.g. the closer chemical environment of a fluorophore. In the field of microscopy this technique is typically referred to as FLIM (Fluorescence Lifetime Imaging Microscopy). Imaging measurements of fluorescence lifetime are further used in the medical field, e.g. for diagnosis on the eye, on the skin or on other organs. By way of example, fundus cameras are employed for medical analysis on the eye. Even if the mentioned medical analysis devices may significantly differ in their form from conventional microscopes they may be generally referred to as microscope-like optical devices.

FLIM measurements are typically performed as an alternative or in addition to intensity-based fluorescence measurements, because additional information concerning the fluorophores and their chemical environment can be gathered therefrom. By way of example, FLIM measurements may be advantageously employed if excitation and emission spectra of different fluorescent dyes differ only slightly. In this case, use can be made of the fact that fluorescent dyes having very similar spectra may have significantly different fluorescence lifetimes. Further, it is possible that unspecific auto-fluorescence signals of the investigated material are superimposed onto the fluorescence signals to be investigated. However, because auto-fluorescence is in most cases, associated with a significantly shorter fluorescence lifetime than, for example, the fluorescence lifetimes of purposefully employed fluorescent dyes, by means of FLIM measurements a distinction between auto-fluorescence, e.g., of a tissue sample, and the fluorescence from fluorescent dyes introduced into the tissue sample can be made. Further, it is possible to investigate auto-fluorescence of biological tissue samples themselves, e.g., to distinguish between healthy and pathologically modified tissue regions.

Further, FLIM measurements can be employed in connection with FRET experiments (FRET: Fluorescence Resonance Energy Transfer), in which energy of an excited molecule can be transferred to another molecule.

In measuring fluorescence lifetimes it is known to use measurement methods working in the time domain, i.e. so-called time-domain methods, or methods working in the frequency domain, i.e. so-called frequency-domain methods.

In the time-domain methods, typically a pulsed laser is used as a source of excitation radiation, which emits pulses in the range of femtoseconds to picoseconds. Then, the fluorescence decay curve is measured on a certain position of the sample. For this purpose, the sample is irradiated with laser light over a period of time which covers a larger number of laser pulses. The fluorescence response of the sample can then be analyzed e.g. using a method on the basis of time-correlated single photon counting. In this case, the time between excitation pulse and detecting the fluorescence photon is measured for each fluorescence photon. With a large number of detected fluorescence photons, a histogram is thereby obtained, which directly represents the fluorescence decay curve. This method can be used e.g. in connection with a confocal laser scanning microscope, in which the sample is scanned for imaging. However, it is also possible to use the method in connection with a wide-field illumination and to use a time-window controlled detection, a so-called "time-gated detection". In this case e.g. a micro-channel plate may be arranged in front of a CCD-array (CCD: Charge Coupled Device). The amplification features of the micro-channel plate can be controlled by temporal variation of amplification voltages in the nanosecond range. In this way it is possible to define time windows for detecting the fluorescence radiation. By using two different time windows it is possible to analyze a mono-exponential decay process. However, the technical implementation of a time-domain method is typically technically complex and cost-intensive.

In the frequency-domain methods, the excitation radiation is periodically modulated, the modulation mostly being sinusoidal with frequencies from the kilohertz range to the gigahertz range. For generating the excitation radiation, e.g. an electro-optical modulator or an acousto-optical modulator in connection with a CW laser (CW: continuous wave) may be used. Alternatively, a laser which is pulsed in the picosecond range may be used.

Both mentioned method types for measuring fluorescence lifetimes are described in more detail in "Handbook of Biological Confocal Microscopy", $2^{nd}$ edition 1995, edited by James B. Poley, Plenum Press.

In European Patent Application, EP 1 162 827 A2, a measurement configuration and a method are proposed, in which the detection process of a CCD sensor is influenced to make possible a phase-sensitive measurement. For generating the excitation radiation, it is proposed to use a blue emitting LED (LED: Light Emitting Diode), which is modulated with frequencies in the kilohertz range. However, the used CCD sensor requires specific modifications, which imply a high outlay and high costs for a practical application in microscopy or medical diagnostics.

In US 2007/0057198 A1, a method for measuring fluorescence lifetimes is described, in which the intensity of the excitation radiation is periodically changed. The method is preferably used in connection with a laser-scanning microscope.

In Schwarte, R., "Dynamic 3D-Vision", International Symposium on Electron Devices for Microwave and Optoelectronic Applications 2001, Vienna, Austria, 15-16 Nov. 2001, the operation of a time-of-flight camera is described, which is referred to as a photonic mixer device (PMD). It is mentioned that such time-of-flight cameras may also be used in the framework of FLIM measurements.

European Patent Application, EP 1 746 410 A1, proposes using a so-called "lock-in imager" in FLIM measurements. The operation of this lock-in imager substantially corresponds to that of a time-of-flight camera. In particular, it is proposed to use a microscope configuration with a dark-field illumination. The excitation radiation is generated by a laser diode or LED.

However, in the known methods for determining fluorescence lifetimes, there are problems in that, in an object under investigation, there are often multiple sources of fluorescence radiation, the fluorescence responses of which are superimposed onto each other. Typically, it is, therefore, merely possible to determine an average fluorescence lifetime of all involved fluorophores.

BRIEF SUMMARY OF THE INVENTION

Accordingly, the invention is based on the object of providing an improved device and an improved method for imaging luminescence measurements, in which a reliable measurement of luminescence lifetimes, in particular fluorescence lifetimes, is possible even if several different decay processes are superposed in the detected luminescence radiation.

According to the invention, this object is solved by a device according to claim 1 and a method according to claim 21. The dependent claims define preferred and advantageous embodiments of the invention.

According to the invention, thus a device and a method for imaging luminescence measurement are provided. The device may specifically be a microscope-like optical device, e.g. a wide-field microscope, a surgical microscope or a fundus camera.

The device according to the invention comprises an electronic pulse generator for generating a periodic modulation signal having rectangular pulses, the pulse duration of the pulses being variably adjustable. Further, the device comprises illumination devices and/or means for illuminating an object under investigation with excitation radiation, the illumination devices and/or means being controlled by the modulation signal for pulse-like modulation of the excitation radiation depending on the modulation signal. Further, the device comprises a time-of-flight camera for phase-sensitive detection of a luminescence response emitted by the object under investigation in response to the excitation radiation, the modulation signal being provided as reference signal to the time-of-flight camera. The luminescence response may specifically be fluorescence radiation, i.e., a fluorescence response, emitted by a material included in the object under investigation. However, it is also possible that it is phosphorescence radiation, i.e., a phosphorescence response, of a material present in the object under investigation.

By using a variably adjustable pulse duration of the modulation signal, it becomes possible to detect a luminescence response for different pulse durations and, thereby, to extend the range of parameters for evaluating the luminescence response. In this way, superimposed luminescence responses having different luminescence lifetimes can be better distinguished from each other. With a corresponding configuration of the evaluation, it is even possible to calculate the respective luminescence lifetimes separately from each other.

In this connection, the device preferably comprises evaluation measures and/or means configured for calculating the luminescence lifetime of at least one material included in the object under investigation depending on a signal strength detected by the time-of-flight camera for a plurality of pulse durations of the modulation signal. For this purpose, preferably at least one luminescence lifetime is calculated on the basis of a normalized modulation depth of the luminescence response determined for different pulse durations of the modulation signal. If there are several materials having unknown luminescence lifetime in the object under investigation, several of these luminescence lifetimes or all luminescence lifetimes can be calculated. In this evaluation, also a phase position of the luminescence response, which is detected by the time-of-flight camera, can be considered, e.g., as a boundary condition. The number of pulse durations used for the evaluation is at least two, however, it is preferably in the range of the number of luminescence lifetimes to be determined or larger. Generally, the precision in determining the luminescence lifetimes can be increased by increasing the number of used pulse durations.

The illumination measures and/or means used in the device according to the invention preferably comprise at least one semiconductor-based radiation source, in particular, a LED. Preferably, multiple semiconductor-based radiation sources are employed, the output radiation thereof being coupled into a single optical path for the excitation radiation. For this purpose, the device preferably comprises measures and/or means for coupling the respective output radiation of the semiconductor-based radiation sources into a common optical path, which are preferably formed by a plurality of color splitters. Alternatively, also a mechanically operated rotational mirror can be used.

The illumination measures and/or means are preferably configured to illuminate the object under investigation in a two-dimensional manner, i.e., there is a spatially distributed wide-field illumination. The time-of-flight camera in this case preferably comprises a plurality of detector elements arranged in a grid-like manner so that a space-resolved detection of the luminescence response is possible. However, the illumination measures and/or means may also be configured for a line-like illumination of the object under investigation, whereby, in this case, in the time-of-flight camera only a line-like arrangement of detector elements may be provided so that the region of the object under investigation which is illuminated in a line-like manner can be detected in a space-resolved manner. The line-like illumination can, for example, be obtained by configuring the illumination measures and/or means in the form of a line scanner. By way of example, a laser beam can be shaped to a narrow line by known methods and can be passed over the sample in a line-like manner by scanner mirrors. However, it is to be understood that, in such a configuration of the illumination measures and/or means, the time-of-flight camera can be provided with a grid-like arrangement of detector elements as well, so as to allow spatial resolution over an extended area region. Further, the illumination measures and/or means can be configured to illuminate the object under investigation with a light blade, which has a plane aligned perpendicular to the plane of an objective used for detecting the luminescence response. This illumination variant is also referred to as SPIM (Selective Plane Illumination Microscopy). In this case, the light blade can also be emulated by a periodically moving laser beam and/or be spatially structured.

In the case of a two-dimensional illumination of the object under investigation the device preferably comprises a radiation homogenizer to spatially homogenize the excitation radiation, so that a uniform illumination is provided for. For this purpose e.g. a hollow bar applied with a reflective coating on the inside and having a quadratic cross section can be used.

Alternatively, a glass bar having a quadratic cross section or one or more microlens arrangements can be used. The radiation homogenizer is preferably configured in such a way that all geometric rays from the radiation source to the investigated object plane have the same value at the object under investigation, so that a homogenous time of flight is provided for the excitation radiation. In this way a temporal smearing of the pulses of the excitation irradiation can be avoided. In this way, the precision in evaluating the luminescence response is increased.

Further, the device preferably comprises at least one multi-band filter for filtering the excitation radiation and/or the luminescence response. In particular, this can be an excitation filter arranged in the optical path of the excitation radiation and a luminescence filter arranged in the optical path of the luminescence response. With these filters, it can be ensured that only the radiation needed for excitation is irradiated onto the sample and that only radiation in the range of the expected luminescence response reaches the time-of-flight camera. Disturbances in detecting the luminescence response which are due to the excitation radiation, e.g., due to glare effects, can be avoided in this way. By using multi-band filters which have multiple pass bands, the device can be adapted to different center wavelengths generated by the illumination measures and/or means, without requiring a mechanical exchange of filters.

Preferably, the device also comprises calibration measures and/or means, which can be introduced into the optical path of the excitation radiation and luminescence response instead of the object under investigation and generate a response radiation having a predetermined phase shift with respect to the excitation radiation. The calibration measures and/or means may, in particular, comprise a semiconductor based radiation source and a photodetector, the semiconductor-based radiation source being controlled to generate a pulse of the response radiation a predetermined time after the photodetector has detected a pulse of the excitation radiation. For this purpose, the semiconductor based radiation source is preferably implemented to be transparent and for example, on the basis of a OLED (Organic Light Emitting Diode). In this case, the photodetector can be positioned, in relation to the optical path of the excitation radiation, behind the semiconductor-based radiation source, so that detecting of pulses of the excitation irradiation and emitting pulses of the response radiation in close positions is rendered possible. Further, the precision of calibration is increased.

The method of measuring luminescence according to the invention comprises the following steps: generating a periodic modulation signal having rectangular pulses, generating excitation radiation, which is modulated in a pulse-like manner depending on the modulation signal, illumination of an object under investigation with the excitation radiation, providing the modulation signal as reference signal to a time-of-flight camera, and phase-sensitive detection of a luminescence response emitted by the object under investigation in response to the excitation radiation for different pulse durations of the modulation signal using the time-of-flight camera. The method preferably further comprises the above-described procedures for operation of the device according to the invention.

In the following, the invention is explained in more detail on the basis of embodiments and by referring to the accompanying drawings.

BRIEF DESCRIPTION OF THE SEVERAL VIEWS OF THE DRAWINGS

FIG. 3 is a set of graphs illustrating signal shapes of excitation radiation and a luminescence response in an exemplary method for measuring luminescence according to the invention.

FIG. 4 is a set of graphs illustrating spectral transmission characteristics of color splitters in the devices according to FIG. 1 and FIG. 2.

DETAILED DESCRIPTION OF THE INVENTION

In the following, the invention is explained in more detail by means of embodiments. These embodiments relate to a wide-field microscope, a fundus camera and a microscope arrangement having SPIM illumination. However, it is to be understood that the described concepts can also be applied in other microscope-like arrangements, e.g. in other types of research and diagnosis microscopes, surgical microscopes, or the like. Even though in the following explanations often reference is made to the special case of fluorescence, it is to be understood that the explanations apply in a corresponding manner also to other forms of luminescence.

Figure 1:
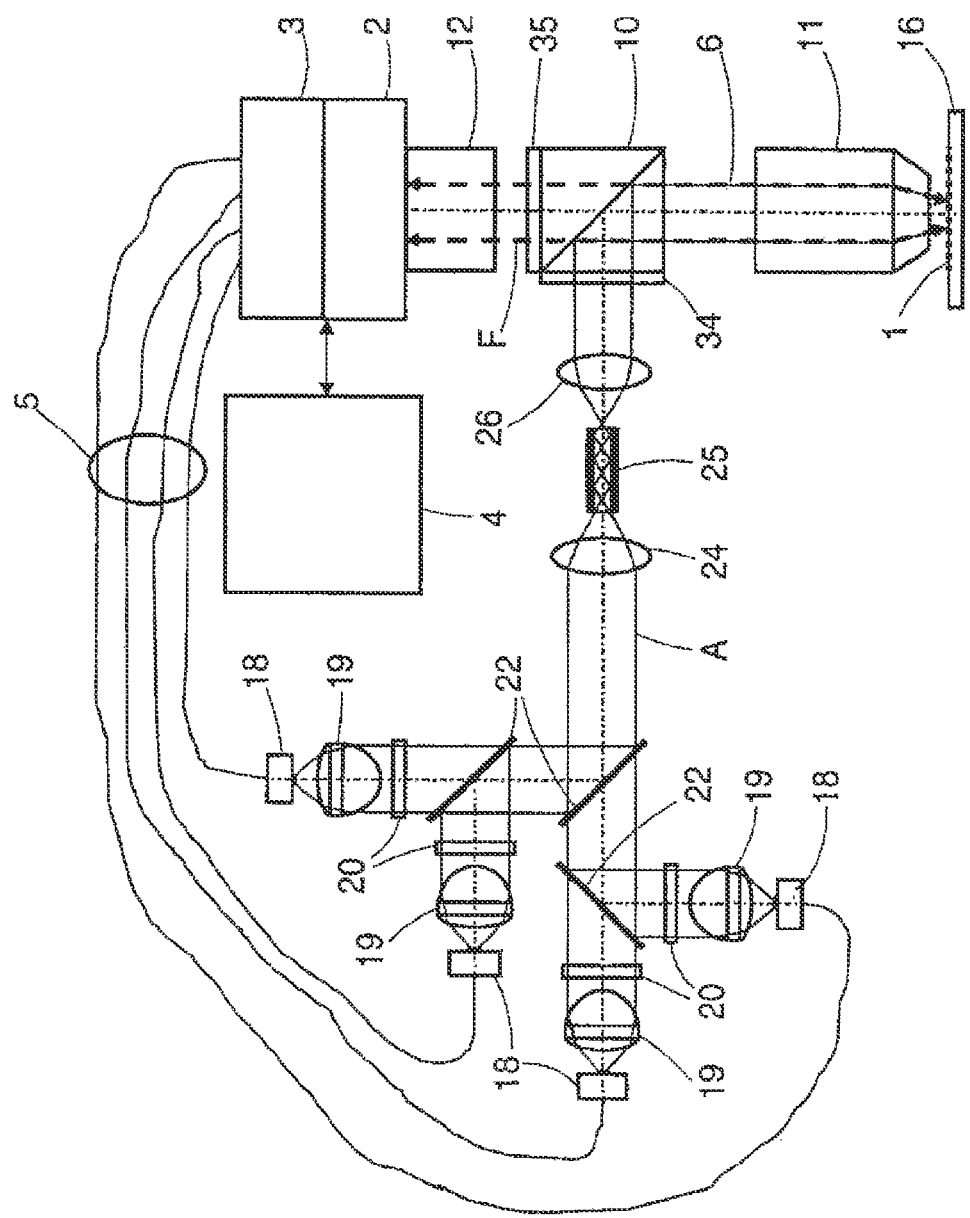
FIG. 1 is a diagrammatic illustration of an exemplary embodiment of a device for measuring luminescence according to the invention, which is in the form of a wide-field microscope.

FIG. 1 shows an optical device for measuring luminescence according to an embodiment of the invention. The device is configured as a vertical wide-field microscope and has the purpose of investigating an object under investigation 1, e.g. a biological or a non-biological sample. In particular, the object under investigation 1 or sample can be biological cells or cell components, DNA, proteins, tissue, human or animal organs, plant components or material surfaces. In the device of FIG. 1, the object under investigation 1 is arranged on a microscope table 16, which for example can be moved in multiple spatial directions in a conventional manner.

The device further comprises illumination measures and/or means, which in the illustrated case are based on four semiconductor-based radiation sources 18 each having a LED. Each of the semiconductor-based radiation sources 18 generates output radiation having a different center wavelength. The output radiation of the semiconductor-based radiation sources 18 is respectively coupled into a common optical path for excitation radiation A via a collimator lens 19, a local excitation filter 20 and a color splitter 22. The collimator lenses 19 preferably are aspherical lenses having a focal length of less than 20 mm. By the collimator lenses 10, the output radiation of the semiconductor-based radiation sources 18 is parallelized. By the local excitation filters 20 undesired spectral branches of the output radiation are cut off. In particular, band-pass filters can be used for this purpose, so that spectral crosstalk by overlapping spectra of the output radiation can be avoided. The semiconductor-based radiation sources 18 each further comprise a current driver which generates the required operating current for generating the output radiation depending on an input signal.

The excitation radiation A is supplied via an input lens 24 to a radiation homogenizer 25 and is coupled out from the radiation homogenizer 25 via an output lens 26. The radiation homogenizer 25 can be a hollow bar applied with a reflective coating on the inside and having a quadratic cross section. Alternatively, also a glass bar having a quadratic cross section or a micro-lens arrangement can be used. The arrangement of the radiation homogenizer 25 and the semiconductor-based radiation sources 18 is configured in such a way that for all geometric rays from the semiconductor-based radiation sources 18 to the investigated object plane of the sample 1 substantially the same light path is obtained, so that no run-time differences occur. In this way, a temporal smearing of pulses of the excitation radiation A can be avoided.

The excitation radiation A coupled out from the radiation homogenizer 25 is supplied via an excitation filter 34 to a dichroitic beam splitter 10, which directs the excitation radiation A via an objective 11 onto the sample 1.

Via the objective 11 further a luminescence response F emitted by the sample 1 in response to the excitation radiation is received and supplied to a time-of-flight camera 2 via the dichroitic beam splitter 10, an emission filter 35 and a detection tube optical system 12. Accordingly, between the dichroitic beam splitter 10 and the sample 1 there is a common optical path 6 of the excitation radiation A and the luminescence response F.

The time-of-flight camera 2 has a two-dimensional arrangement of detector elements which are each referred to as a pixel and allow for a specially resolved detection of the luminescence response F. The arrangement in the form of a regular grid or a matrix comprises at least 100 pixels, typically 128×128 or 256×256 pixels. The number of pixels can be selected depending on the desired spatial resolution.

Each of the detector elements of the time-of-flight camera 2, i.e. each pixel, is configured for phase-sensitive detection of the luminescence response. This means that the phase position of the luminescence response in relation to a reference signal and typically also the modulation amplitude of the luminescence response at the frequency of the reference signal are detected. The time-of-flight camera 2 can be a commercially available time-of-flight camera, which for each pixel outputs a distance value and an intensity corresponding to the modulation amplitude. By using a commercially available time-of-flight camera 2, the costs for the overall arrangement can be reduced.

Further, the device comprises an electronic pulse generator 3, which in FIG. 1 is in close vicinity to the time-of-flight camera 2. The pulse generator 3 generates a periodic modulation signal having rectangular pulses. The modulation signal 3 is supplied as reference signal to the time-of-flight camera 2. Further, the modulation signal is supplied via high-frequency compliant signal lines 5 to the semiconductor-based radiation sources 18, which, in this way, are controlled by the modulation signal. For example, the signal lines 5 can be coaxial lines. By way of example, the pulse generator 3 is implemented by an electronic chip, e.g., an FPGA chip (FPGA: Field Programmable Gate Array) or a CPLD chip (CPLD: Complex Programmable Logic Device).

The current drivers of the semiconductor-based radiation sources 18 receive the modulation signal via the signal lines 5 and generate the operating current for the respective LED in such a way that the output radiation of the semiconductor-based radiation sources 18 comprises pulses as well, the length and shape of which substantially correspond to that of the modulation signal. Alternatively, the current drivers for the semiconductor-based radiation sources 18 can also be arranged within the signal generator 3. However, the arrangement of the current drivers within the semiconductor-based radiation sources 18 provides the advantage that only low power signals need to be transferred over longer distances. The requirements on the signal lines 5 can therefore be reduced. In view of their dynamic capacity, the semiconductor-based radiation sources 18 are designed in such a way that they can be modulated with rise times of less than 1 μs, preferably less than 10 ns. Here, the time-averaged output radiation power is at least 10 mW, preferably at least 100 mW.

The device further comprises a control and evaluation device 4 which accomplishes control of the essential functions of the device. In particular, the control and evaluation device 4 controls the functions of the time-of-flight camera 2 and of the pulse generator 3 through corresponding control signals. For evaluation purposes, the control and evaluation device 4 further receives the signals detected by the time-of-flight camera 2, in particular a distance signal and an intensity signal for each pixel of the time-of-flight camera 2. Further, the control and evaluation device 4 can also control further functions of the device, e.g. an automatic drive of the microscope table 16 and an automatic focusing of the objective 11. The control and evaluation device can be a micro-processor-based system, in particular a computer system with corresponding input and output devices and memory devices. The control at evaluation device 4 can also be adapted for operation of the device via a graphical user interface.

The control of the semiconductor-based radiation sources 18 via the pulse generator 3 is accomplished in such a way that each of the semiconductor-based radiation sources 18 can be controlled individually with variably adjustable intensity and variably adjustable pulse duration. The use of variably adjustable pulse durations in the evaluation of luminescence lifetimes is explained in more detail below. The pulse durations are preferably in the range of below 100 ms to below 1 ns, in particular in the range from 1 ns to 100 μs. The modulation frequency is typically at least 1 MHz, preferably about 10 MHz.

The center wavelengths of the semiconductor-based radiation sources shown in FIG. 1 can for example be selected in such a way that a first semiconductor-based radiation source has a center wavelength in the range of 600-650 nm, a second semiconductor-based radiation source 18 has a center wavelength in the range of 500-550 nm, a third semiconductor-based radiation source 18 has a center wavelength in the range of 450-490 nm, and a fourth semiconductor-based radiation source has a center wavelength in the range of 350-410 nm. At each of these center wavelengths effective LEDs are available, and a large portion of the known fluorescent dyes can be covered. However, the use of other center wavelengths, e.g. in a range between 200 nm and 2000 nm, is conceivable as well.

In the device of FIG. 1, the output radiation of the semiconductor-based radiation sources 18 is coupled via the three color splitters 22 into a single optical path. With an increased or decreased number of semiconductor-based radiation sources, the number of used colors splitters 22 is to be adjusted in a corresponding manner. Generally, for coupling in the output radiation of n semiconductor-based radiation sources 18, a number of n−1 color splitters 22 is needed.

The semiconductor-based radiation sources 18 can each be individually controlled with a variably adjustable intensity so that by mixing the respective output radiation of the semiconductor-based radiation sources 18 a flexibly adjustable spectrum of the excitation radiation can be obtained.

The transmission spectra of the color splitters 22 are preferably adapted to the center wavelengths of the semiconductor-based radiation sources 18 in such a way that a maximum of radiation power is coupled into the common optical path. In the case of the color splitters 22 simple dichroites for an irradiation angle of 45° can be used, so that for each color splitter substantially an edge of the transition from maximum reflection to maximum transmission is to be adapted. The use of other color splitters having other irradiation angles and/or multiple edges is conceivable as well.

As an alternative to coupling the respective output radiation of the semiconductor-based radiation sources 18 into the common optical path, the semiconductor-based radiation sources 18 can also be arranged on a circle having a rotational minor in its center. The radiation of each semiconductor-based radiation source 18 then can be coupled into the common optical path by corresponding positioning of the rotational mirror. However, in this case it is only possible to use the output radiation of one semiconductor-based radiation source 18 for exciting the sample 1. Further, when using the color splitters 22 a faster electronic switching between different excitation spectra can be done. A combined solution of rotational minor and color splitters is conceivable as well.

In the device of FIG. 1, the semiconductor-based radiation sources 18 each comprise a LED. However, it is also possible to use other semiconductor light sources, e.g. semiconductor lasers. When using a semiconductor laser for a two-dimensional wide-field illumination, a rotating scattering plate or equivalent element can be provided in the optical path of the excitation radiation to thereby avoid so-called speckle structures in the wide-field illumination.

The device can additionally comprise further light sources, which are not shown in FIG. 1, in particular, a light source for generating substantially white light, e.g., a white LED, a white laser, a flash lamp, a halogen lamp, or an arc lamp. By way of example, the output radiation of this further light source can be coupled in by an articulated mirror in front of the radiation homogenizer 25. By way of example, the further light source can then be advantageously employed when the needed center wavelength for a luminescence excitation cannot be delivered with sufficient power by the semiconductor-based radiation sources. In the case of the further light source comprising, for example, a halogen lamp or an arc lamp and not being capable of fast electronic modulation, an additional light modulator can be provided for this further light source, e.g., in the form of an electro-optical modulator or an acousto-optical modulator. This modulator would then, as well, be controlled by the modulation signal generated by the pulse generator 3. In this connection, it is also possible to couple in the output radiation emitted by the further light source via a fiber optical wave guide, a fiber strand or a liquid light guide. For example, problems due to an excessive heat generation by the further light source can be avoided in this way.

Figure 2:
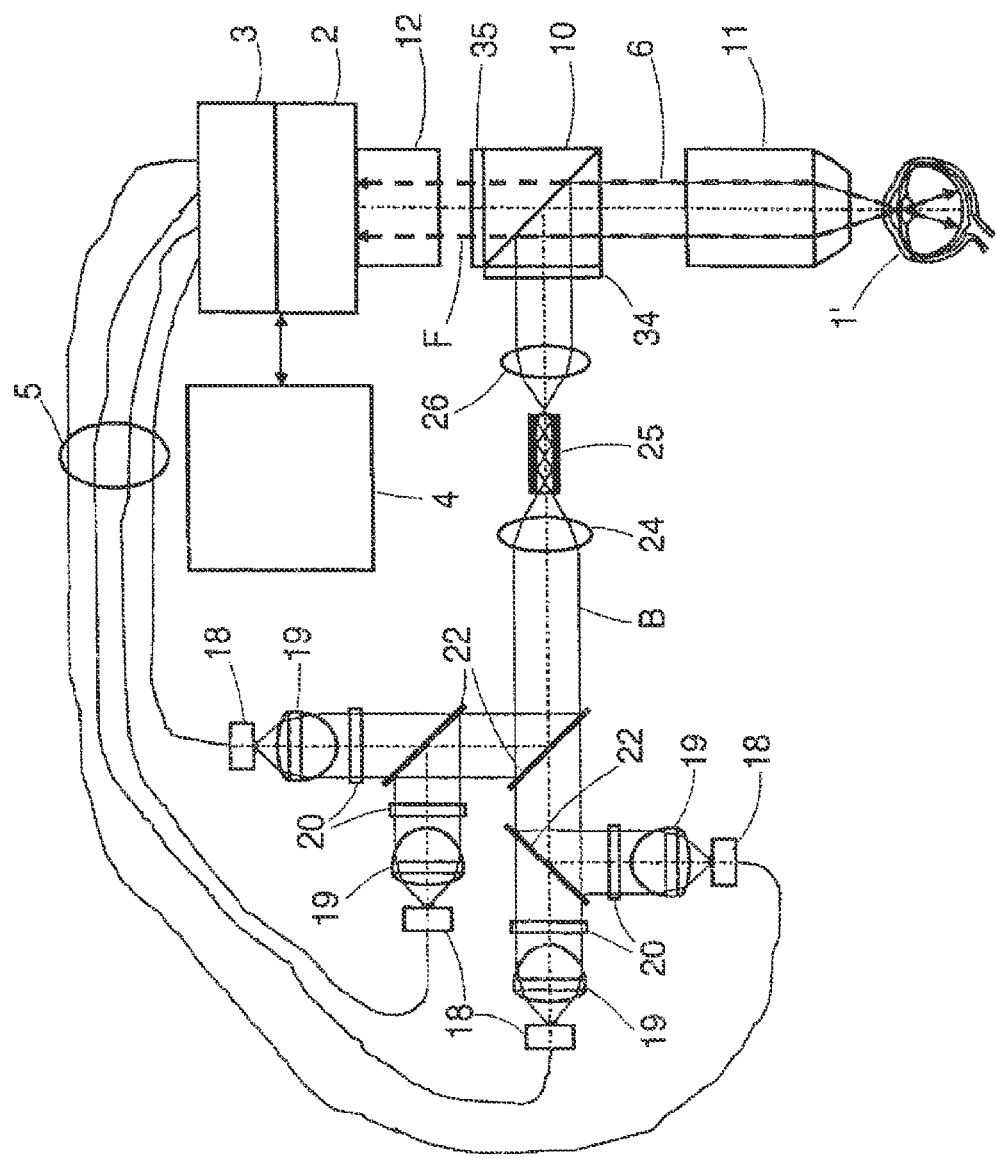
FIG. 2 is a diagrammatic illustration of an exemplary embodiment of a device for measuring luminescence according to the invention in the form of a fundus camera.

FIG. 2 schematically illustrates a device according to a further embodiment of the invention. With regard to its components, the device of FIG. 2 substantially corresponds to the device of FIG. 1, so that in this connection reference can be made to the corresponding explanations in relation to FIG. 1.

However, as compared to the device of FIG. 1, the device of FIG. 2 is not configured as a wide-field microscope, but as a fundus camera. A fundus camera typically has the purpose of investigating the ocular fundus, i.e. in this case the object under investigation or sample 1 is e.g. a human eye.

In the case of the fundus camera of FIG. 2, the center wavelengths of the semiconductor-based radiation sources 18 are preferably selected in such a way that one semiconductor-based radiation source has a center wavelength in the range of 750 to 800 nm, e.g. for excitation of indocyanine green, that one semiconductor-based radiation source 18 has a center wavelength in the range of 500 to 550 nm, e.g. for excitation of tissue autofluorescence, that one semiconductor-based radiation source 18 has a center wavelength in the range of 450-500 nm, e.g. for excitation of fluorescein or melanin, and that one semiconductor-based radiation source 18 has a center wavelength in the range of 400-490 nm, e.g. for excitation of lipofuscin. However, this selection of the center wavelengths is only exemplary, and it is to be understood that the center wavelengths can each be coordinated with the endogenic or exogenic fluorophores to be investigated. Typical exogenic fluorophores for fluorescence angiography on the eye are fluorescein and indocyanine green. An overview of endogenic fluorophores in the eye and their clinical relevance can be found, e.g., in "Tau mapping of the autofluorescence of the human ocular fundus", Schweitzer et al., Proc. SPIE Vol. 4164, p. 79-89, Laser Microscopy, Karsten Koenig; Hans J. Tanke; Kerbert Schneckenburger; Eds.

A disease pattern relevant for clinical investigations is for example the age-related macula degeneration, in which the concentration of lipofuscin in the ocular fundus is an important indicator.

FIG. 3 illustrates in an exemplary manner signal courses of the excitation radiation A and the luminescence response F. In FIG. 3 the time axis is designated by t. In FIG. 3, it can be seen that the luminescence response F is modulated with the same frequency as the excitation radiation A, but the pulses of the luminescence response are deformed in relation to the rectangular pulses of the excitation radiation A. In particular, a center shift of the pulses in the direction of the time axis results, which corresponds to an effective delay. This delay as well as the associated modulation amplitude of the luminescence response F can be detected by the time-of-flight camera 2 of the devices as shown in FIGS. 1 and 2.

FIG. 4 schematically illustrates exemplary transmission spectra T of the color splitters 22 in the devices of FIGS. 1 and 2. Further illustrated are exemplary spectral distributions of the output radiation emitted by the semiconductor-based radiation sources 18. In FIG. 4 (A) the edge of the color splitter 22 is arranged in such a way that only for the semiconductor-based radiation source having the largest center wavelength the spectral distribution of the output radiation is in the pass band of the color splitter 22. In FIG. 4 (B) the edge of the color splitter 22 is arranged in such a way that for both of the semiconductor-based radiation sources having the highest center wavelengths the spectral distributions of the output radiation are within the pass band of the color splitter 22. In FIG. 4 (C) the edge of the color splitter 22 is arranged in such a way that for the semiconductor-based radiation sources 18 having the three highest center wavelengths the spectral distributions of the output radiation are within the pass band of the color splitter 22. The respective output radiation of the semiconductor-based radiation sources can therefore be effectively coupled into the common optical path for the excitation radiation A. Spectral parts which are not transmitted are largely completely reflected by the color splitters 22.

Figure 5:
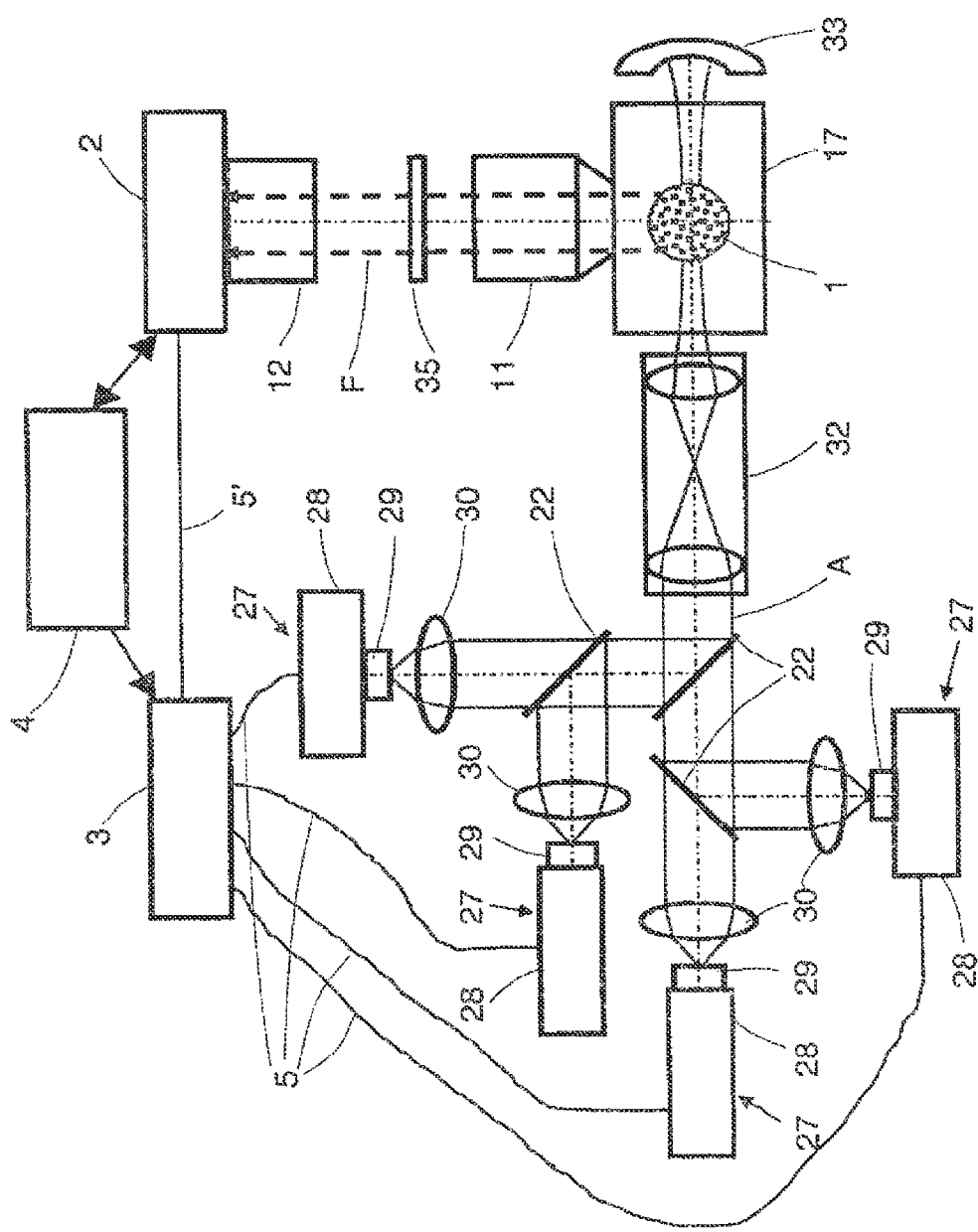
FIG. 5 is a diagrammatic illustration of an exemplary embodiment of a device for measuring luminescence according to the invention having SPIM illumination.

FIG. 5 shows a further embodiment of a device for measuring luminescence in the form of a microscope having SPIM illumination. Components of the device of FIG. 5 which correspond to those of the devices of FIGS. 1 and 2 have been designated by the same reference signs, and their detailed explanation is omitted at this point. Rather, reference is made to the corresponding explanations with respect to FIGS. 1 and 2.

Deviating from the devices of FIGS. 1 and 2, the device of FIG. 5 uses SPIM illumination. In this case semiconductor-based radiation sources 27 are used, which comprise laser diodes 29. Further, the semiconductor-based radiation sources 27 each comprise a current driver 28 having a feedback device based on a photodiode. The semiconductor-based radiation sources 27 of the device of FIG. 5 are arranged in a similar manner as the semiconductor-based radiation sources 18 of the devices of FIGS. 1 and 2, and their output radiation is coupled into a common optical path for the excitation radiation A via correspondingly adapted collimator lenses 30 and color splitters 22.

In this optical path there is a telescopic optical system 32, which causes a reduction of the beam cross-section of the laser radiation. Here, the reduction in the direction of the axis of the objective 11 is significantly stronger than perpendicular to the axis, so that a light blade is generated. For this purpose, the telescopic optical system includes an anamorphotic lens system. Further, a concave mirror 33 is provided, by which the light blade of the excitation radiation is reflected into itself. In this way, symmetry of illumination can be increased. Alternatively, it is possible that the excitation radiation is split with beam splitters and irradiated onto the object under investigation from multiple sides.

The sample, which can be living microorganisms, is typically embedded in a cylinder shaped gel, the cylinder axis typically being substantially perpendicular to the axis of the objective 11. To avoid drying of the gel, the cylinder can be maintained in an aqueous solution, which is located in a tank 17.

The luminescence response F is again detected via the objective 11 and provided via the emission filter 35 and the detection tube optical system 12 to the time-of-flight camera 2.

The current drivers 28 of the semiconductor-based radiation sources 27 are preferably configured in such a way that they have a very low current rise time of about 1 ns or less. To avoid the laser diodes 29 of the semiconductor-based radiation sources 27 not being switched into a completely currentless state in fast periodic switching processes, the current drivers 27 each also comprise a photodiode or another photodetector, through which the optical power emitted by the laser diode 29 is detected. The output signal of the photodiode 29 is used as a feedback signal for controlling the output power of the laser diode 29.

Further, in the device of FIG. 5 the time-of-flight camera 2 is connected via a signal line 5' with the pulse generator 3. In this way the signal lines 5 to the semiconductor-based radiation sources 27, of which several are required, can be shortened. Further it is also possible that the pulse generator is directly connected to the time-of-flight camera 2 as shown in FIGS. 1 and 2. Conversely, also in the devices of FIGS. 1 and 2 the pulse generator 3 can be arranged closer to the semiconductor-based radiation sources 18, and a further high-frequency compliant signal line 5' be used, as it is shown in FIG. 5. For example, the further high-frequency compliant line 5' can be a coaxial line.

In the following, a method for evaluating luminescence lifetimes, in particular fluorescence lifetimes, according to an embodiment is further explained.

As already mentioned, the time-of-flight camera 2 of the devices shown FIGS. 1, 2 and 5 provide a distance value X for each pixel. This distance value is derived from the phase position of the detected luminescence response in relation to the reference signal supplied to the time-of-flight camera 2. In particular, the following relation applies for the output distance:

$$X = \left(\frac{\Delta\varphi}{2\pi}\right)\frac{c_0 T}{2}, \quad (1)$$

$\Delta\varphi$ being the phase shift, $c_0$ the vacuum light speed, and T the cycle duration of the reference signal.

This distance value is converted to a runtime $t_R$ according to the relation.

$$t_R = \frac{2X}{c_0}. \quad (2)$$

In the above relations, it was assumed in a simplifying manner that the excitation radiation A and the luminescence response F propagate in vacuum. However, this assumption is not fulfilled in general, because the excitation radiation A and the luminescence response F propagate in the optical path of a microscope-like arrangement. In this case, the propagation speed is influenced by the used optical elements, such as lenses, beam splitters, color splitters etc. This can be taken into consideration in the context of a calibration, which will be further explained below.

In the method first a runtime offset $t_{off}$ is determined, which includes all phase shifts which cannot be attributed to the luminescence lifetime. In particular, the runtime offset is caused in part by the signal lines 5 between the pulse generator 3 and the semiconductor-based radiation sources 18, 27 and by the optical paths in the microscope-like arrangement. For determining the runtime offset, e.g. a mirror or a thin, typically a few micrometers thick, fluorescent layer with precisely known fluorescence lifetime can be introduced into the optical path of the excitation radiation A and of the luminescence response F, in particular into the object plane, instead of the sample 1, 1'. As calibration samples having a known fluorescence lifetime, strongly diluted solutions of the dyes R6G or Cy5 can be used, which are introduced into the object plane in a layer of a few micrometers thickness. When using a mirror, the emission filter 35 must be removed where necessary. With this calibration arrangement the runtime can be measured for each pixel of the time-of-flight camera 2. When using a mirror, the runtime offset $t_{off}$ immediately results from the runtime measured in this way. When using a fluorescent layer, the runtime offset is equal to the measured runtime minus the known fluorescence lifetime.

In a luminescence measurement on a fluorescent or phosphorescent sample the average fluorescence lifetime τ is now determined on the basis of the relation $$\tau = t_R - t_{off}. \quad (3)$$

In the case of a mono-exponential decay process of the fluorescence, the average fluorescence lifetime determined in this way can be used as end result for the fluorescence lifetime.

In the case of a multi-exponential decay process of the luminescence, which is typical when multiple fluorophores or luminescent materials are present, the luminescence radiation of which is superimposed in the luminescence response F, the luminescence lifetime however cannot be determined on the basis of the simple relation of equation (3). An exemplary multi-exponential decay process of a luminescence response is shown in FIG. 6.

Figure 6:
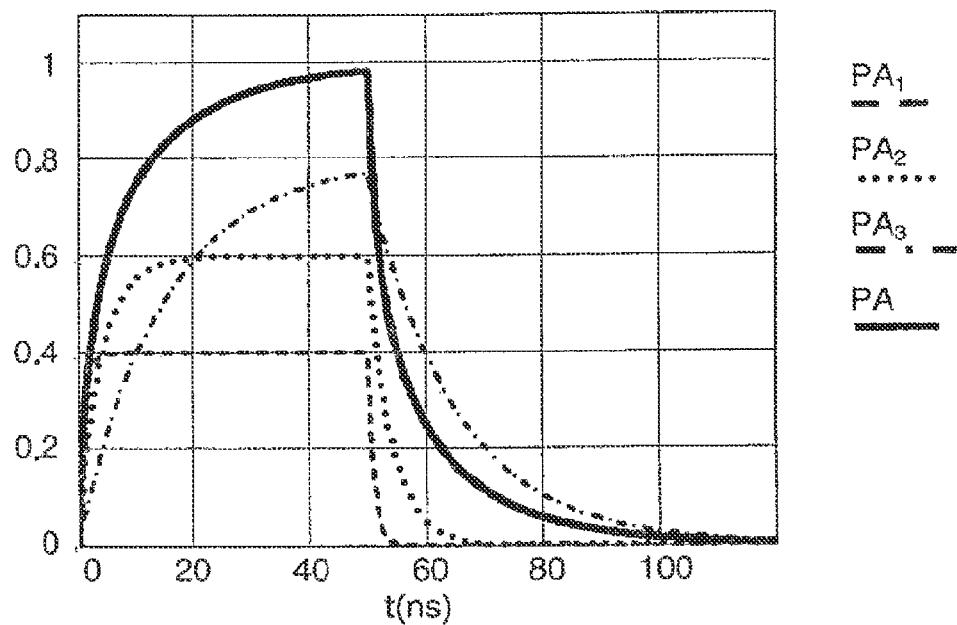
FIG. 6 is a graph illustrating an exemplary temporal course of a pulse of a luminescence response in a method for measuring luminescence according to the invention.

In particular, FIG. 6 shows the individual fluorescence responses of the different fluorophores in the form of a dashed, a dotted and a dash-dotted line, as well as the combined total fluorescence response in the form of a solid line. The shown temporal signal courses can be modeled by means of piece-wise composed exponential functions:

A substantially rectangular pulse of the excitation radiation A can be modeled by $$PE(t) = F_E \left[ \left(1 - e^{-\frac{t}{\tau_E}}\right) - \Phi(t - \Delta t)\left(1 - e^{-\frac{t-\Delta t}{\tau_E}}\right) \right], \quad (4)$$

$\Phi(t-\Delta t)$ being the unit step function and $\tau_E$ being selected very small so as to emulate the steep edges of the rectangular pulse. By way of example, a value of 0.01 ms can be selected for $\tau_E$. The pulse duration is denoted by $\Delta t$.

In a corresponding manner, the fluorescence responses F of the three different fluorophores can be modeled by the expressions $$PA_1(t) = F_1 \left[ \left(1 - e^{-\frac{t}{\tau_1}}\right) - \Phi(t - \Delta t)\left(1 - e^{-\frac{t-\Delta t}{\tau_1}}\right) \right] \quad (5)$$

$$PA_2(t) = F_2 \left[ \left(1 - e^{-\frac{t}{\tau_2}}\right) - \Phi(t - \Delta t)\left(1 - e^{-\frac{t-\Delta t}{\tau_2}}\right) \right] \quad (6)$$

$$PA_3(t) = F_3 \left[ \left(1 - e^{-\frac{t}{\tau_3}}\right) - \Phi(t - \Delta t)\left(1 - e^{-\frac{t-\Delta t}{\tau_3}}\right) \right]. \quad (7)$$

Here, $\tau_1$ denotes the fluorescence lifetime of the first fluorophore, $\tau_2$ denotes the fluorescence lifetime of the second fluorophore, and $\tau_3$ denotes the fluorescence lifetime of the third fluorophore. The fluorescence amplitudes are respectively denoted by $F_1$, $F_2$, and $F_3$.

Accordingly, the resulting normalized combined total fluorescence response is $$PA(t) = \frac{PA_1(t) + PA_2(t) + PA_3(t)}{F_1 + F_2 + F_3}. \quad (8)$$

This total fluorescence response is associated with an average lifetime which corresponds to a weighted average value of the three individual fluorescence lifetimes $\tau_1$, $\tau_2$ and $\tau_3$ with the individual fluorescence amplitudes $F_1$, $F_2$, and $F_3$ as weight factors:

$$\tau = \frac{F_1 \cdot \tau_1 + F_2 \cdot \tau_2 + F_3 \cdot \tau_3}{F_1 + F_2 + F_3}. \quad (9)$$

Generally, for an arbitrary number of different fluorophores or luminescent materials, the average luminescence lifetime can therefore be expressed as $$\tau = \frac{\sum_i F_i \cdot \tau_i}{\sum_i F_i}. \quad (10)$$

The fluorescence amplitudes $F_1$, $F_2$, and $F_3$ depend on the concentration of the fluorophore, the extinction coefficient, the quantum efficiency of fluorescence, and the detection sensitivity of the overall arrangement. As can be seen from equations (4) to (7), in this case fluorescence amplitude is to be understood as the maximum amplitude of the fluorescence response in the stationary state, e.g. for an excitation with an excitation radiation of constant intensity. However, when using pulse-like modulated excitation radiation, this maximum value is not reached so that the signal amplitude actually occurring in the fluorescence response is smaller than the maximum fluorescence amplitude. Accordingly, a normalized modulation depth, which is always smaller than one for finite pulse durations, can be determined through the relation of the actual amplitude of the fluorescence response to the maximum fluorescence amplitude.

Mathematically it can now be shown that the measured average luminescence lifetime is independent of the pulse duration of the excitation radiation. Accordingly, a method is proposed for determining the individual luminescence lifetimes, which in the first instance is based on an evaluation of the signal strength or intensity, e.g. the amplitude of the luminescence response, detected by the time-of-flight camera 2.

For the amplitudes of the fluorescence response as a function of the pulse duration the following relations result for the individual fluorophores of FIG. 6

$$PA_{1max}(\Delta t) = F_1\left(1 - e^{-\frac{\Delta t}{\tau_1}}\right) \quad (11)$$

$$PA_{2max}(\Delta t) = F_2\left(1 - e^{-\frac{\Delta t}{\tau_2}}\right) \quad (12)$$

$$PA_{3max}(\Delta t) = F_3\left(1 - e^{-\frac{\Delta t}{\tau_3}}\right). \quad (13)$$

Generally, for an arbitrary number of fluorophores or luminescent materials, the amplitude of the luminescence response can therefore be expressed by $$PA_{imax}(\Delta t) = F_i\left(1 - e^{-\frac{\Delta t}{\tau_i}}\right). \quad (14)$$

For the total fluorescence response, which can actually be measured, the maximum amplitude is therefore given by $$PA_{max}(\Delta t) = PA_{1max}(\Delta t) + PA_{2max}(\Delta t) + PA_{3max}(\Delta t), \quad (15)$$

or more generally for an arbitrary number of fluorophores or luminescent materials by $$PA_{max}(\Delta t) = \sum_i PA_{imax}(\Delta t). \quad (16)$$

The normalized modulation depth of the total luminescence response can therefore be approximated by $$MPA(\Delta t) = \frac{PA_{max}(\Delta t)}{PA_{max}(\Delta T)}, \quad (17)$$

$PA_{max}(\Delta T)$ denoting the amplitude of the total luminescence response for a pulse duration which is significantly larger than the maximum expected fluorescence lifetime. For example, the pulse duration $\Delta T$ can be selected several orders of magnitude above the maximum expected luminescence lifetime, e.g. in the range of microseconds to milliseconds.

Figure 7:
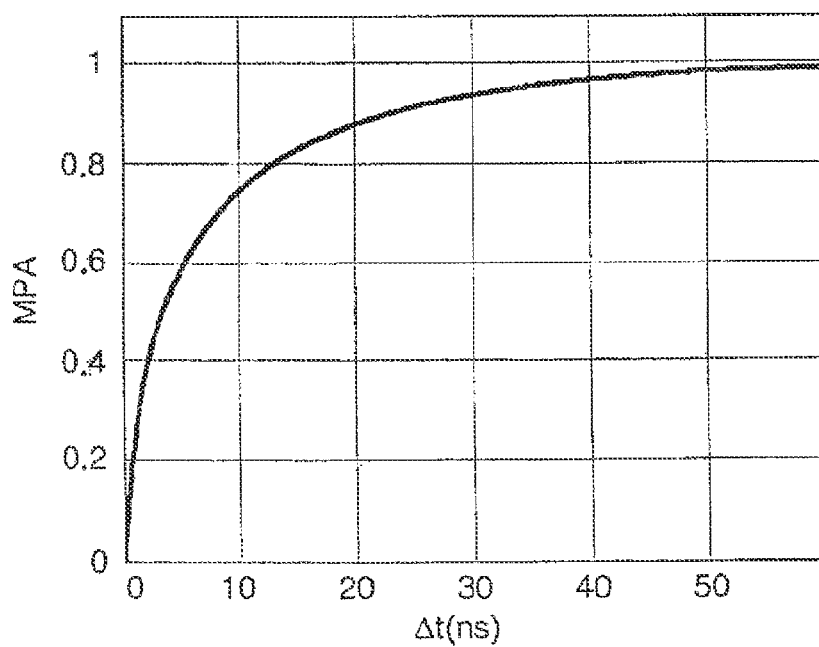
FIG. 7 is a graph illustrating an exemplary course of a normalized modulation depth depending on the pulse duration in a method for measuring luminescence according to the invention.

An exemplary course of the normalized modulation depth as a function of the pulse duration is shown in FIG. 7. This course is characteristic for the underlying luminescence lifetimes and luminescence amplitudes. With sufficiently precise measurement of the course of the normalized modulation depth as a function of the pulse duration, the parameters to be found, in particular the luminescence lifetimes to be found, can be determined.

Figure 8:
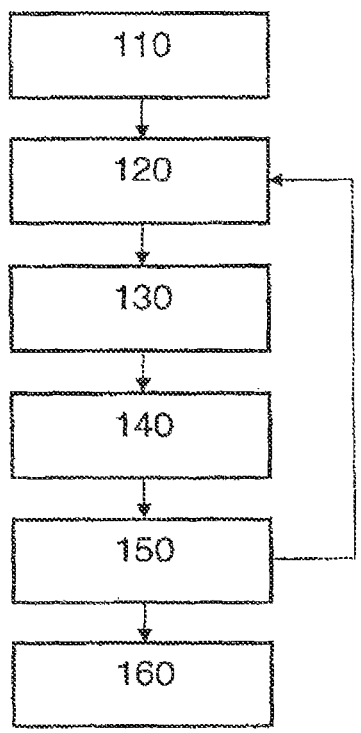
FIG. 8 is a flowchart for illustrating a method of measuring luminescence according to an exemplary embodiment of the invention.

FIG. 8 shows a flow chart which schematically illustrates a method for determining the fluorescence lifetimes by evaluating the luminescence response for different pulse durations.

In step 110 the amplitude of the luminescence response is measured in the quasistationary state, e.g. with a pulse duration $\Delta T$ which is significantly larger than the expected fluorescence lifetimes. Result of this measurement thus is the total luminescence amplitude, e.g. the sum of the individual luminescence amplitudes. For the example explained in connection with FIGS. 6 and 7 this quantity corresponds to the sum $F_1+F_2+F_3$.

In step 120, now a pulse duration in the range of the expected luminescence lifetimes is selected for the modulation signal, and the amplitude of the luminescence response is measured.

In step 130, the amplitude measured in this way is normalized to the measured total luminescence amplitude, i.e. the normalized modulation depth is determined.

In step 140, another pulse duration is selected, and in step 150 the steps 120 to 140 are repeated for a given number of pulse durations. It has turned out that a number of repetitions is advantageous which substantially corresponds to the number of unknown luminescence lifetimes to be determined. However, by a further increased number of repetitions the precision of the evaluation can be further increased.

In step 160, numerical fitting of the modulation depths obtained in this way is accomplished on the basis of equations (16) and (17). In this connection different suitable numerical fitting methods can be employed, in which the parameters $\tau_i$ and $F_i$ are varied until a given agreement with the calculated values of the modulation depth is reached. For example, this method can use as a criterion for assessing the agreement that the sum of the quadratic deviations becomes minimal or falls below a predetermined relative or absolute threshold value.

The precision of the described method can be further improved if available additional information is introduced into equations (16) and (17), for example known luminescence lifetimes $\tau_i$ or known luminescence amplitudes. Further, the measured average luminescence lifetime $\tau$ according to equation (9) can be used as a boundary condition.

In the method, the pulse repetition frequency can be held constant while varying the pulse duration, or can be varied as well. However, it is advantageous to increase the pulse repetition frequency with decreasing pulse duration so that the yield of luminescence photons in the luminescence response is increased. The time between two pulses of the excitation radiation should be larger than the largest expected luminescence lifetime. Accordingly, it is particularly advantageous if not only the pulse duration of the modulation signal generated by the pulse generator 3 can be variably adjusted, but also the frequency or pulse-duty ratio.

Figure 9:
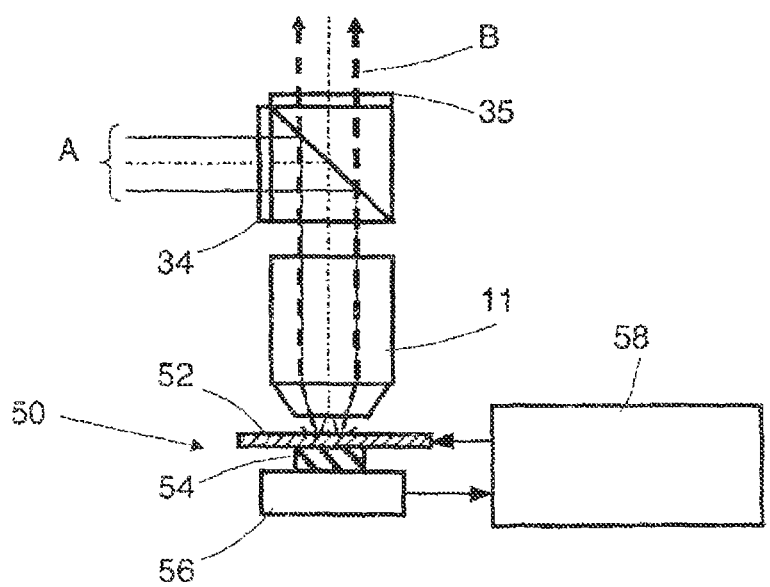
FIG. 9 is a diagrammatic illustration of an exemplary embodiment of a calibration device for use in connection with a device for measuring luminescence according to the invention.

FIG. 9 shows a calibration device which can be used in connection with the above-described concepts. The calibration device is configured to be introduced into the optical path of the excitation radiation A and the luminescence response instead of the object under investigation 1, 1'. In particular, this device can be used in the devices as explained in connection with FIGS. 1 and 2. However, it can also be adapted for use with the device as shown in FIG. 5.

The calibration device 50 of FIG. 9 comprises a semiconductor-based radiation source 52, which preferably is implemented on the basis of a transparent OLED and has the form of a thin layer. Accordingly, it is a thin electronically controllable radiation source. The layer thickness is 1 µm or less. With respect to the optical path arranged behind the semiconductor-based radiation source 52, the calibration device 50 further comprises a photodetector, which can for example comprise a photodiode 54 and a corresponding signal amplifier 56. An output signal of the photodetector is supplied to a control 58 which evaluates the output signal of the photodetector and, depending thereon, provides a control signal to the semiconductor-based radiation source 52. In particular, the control unit 58 is configured in such a way that, after an adjustable predetermined delay time after detecting a pulse in the excitation radiation A by the photodetector, it controls the semiconductor-based radiation source 52 to emit a pulse of a response radiation B.

Figure 10:
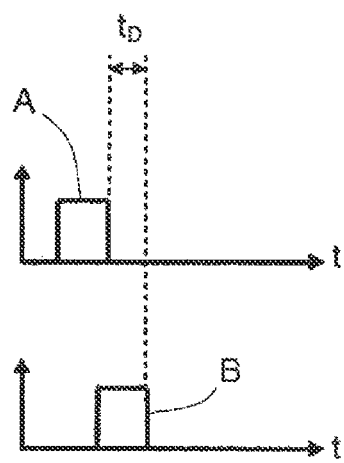
FIG. 10 is a set of graphs illustrating the temporal position of a pulse of the excitation radiation in relation to a pulse of the response radiation in a calibration method according to an exemplary embodiment of the invention.

The chronology of pulses of the excitation radiation A and pulses of the response radiation B is schematically shown in FIG. 10, in which t again denotes the time. The adjustable delay time is denoted by $t_D$.

The advantage in using the calibration device as explained in connection with FIG. 9 is that no luminescence reference sample is needed for an efficient and precise calibration. Accordingly, problems with respect to sensitivity of reference samples to environmental conditions, such as pH value, solvent used, temperature etc., are avoided. When using an OLED in the semiconductor-based radiation source 52, a further resulting advantage is that the radiation is emitted from a very thin layer, which is very similar to the typical investigated samples. In addition, a very homogenous two-dimensional irradiation can be obtained by an OLED, which also provides for a high spatial homogeneity of the calibration in a microscope-like optical device with two-dimensional detection of the luminescence response. The used semiconductor-based radiation source 52 is preferably selected to emit a wavelength spectrum transmitted by the emission filter 35 used. Accordingly, although not necessary, emission filter 35 can be removed from the optical path for the calibration process.

Figure 11:
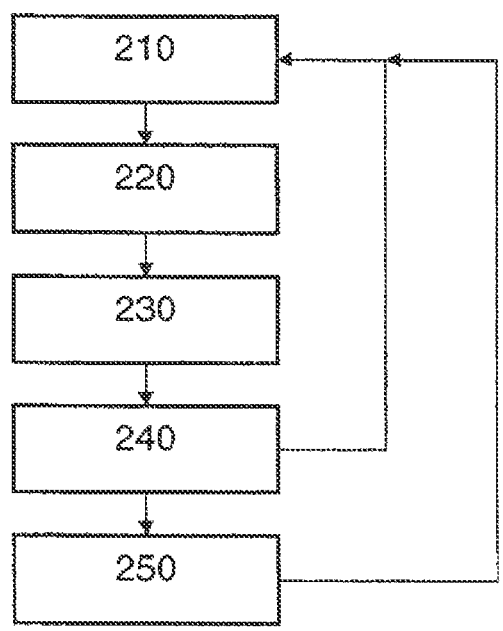
FIG. 11 is a flowchart for illustrating a calibration method in a method of measuring luminescence according to an exemplary embodiment of the invention.

A calibration method which is based on the above-described concepts and on the calibration device 50 as shown in FIG. 9 is schematically illustrated by the flow chart of FIG. 11.

In step 210, a pulse-like modulated excitation radiation A is emitted by one or more of the semiconductor-based radiation sources 18, 27 provided for generating the excitation radiation A. The pulse-like modulated excitation radiation A is directed onto the calibration device 50, which is situated at the position in which the sample to be investigated 1, 1' is situated during normal measurement operation.

In step 220, a pulse of the excitation radiation A is detected by the photodetector, e.g. on the basis of its negative edge. The control unit 58 now effectuates that the pulse of the response radiation B is emitted after the adjusted delay time $t_D$, which simulates a time-delayed luminescence response. For this purpose, the pulse of the response radiation B preferably has the same length as the pulse of the excitation radiation A. The delay time $t_D$, can be in the range of about 0.1 ms to 50 ms and corresponds to a simulated average luminescence lifetime. For measuring a luminescence response from metastable states, the delay time $t_D$, can also be increased into the range of 1 ms or more for the calibration measurement.

In step 230, the pulse of the response radiation is detected by the time-of-flight camera 2 and used for determining a simulated luminescence lifetime.

In step 240, the steps 210 to 230 are repeated until the desired measurement precision for the simulated luminescence lifetime is obtained by averaging. For example, 10,000 repetitions can be used here.

In step 250, the steps 210 to 240 are repeated for other adjusted delay times $t_D$. In this way, for example non-linearities of the runtime measurement can be eliminated in a calculatory manner.

In the calibration device 50 as shown in FIG. 9, a LED or a laser diode can be used instead of an OLED. However, since these are typically non-transparent it is then advantageous to produce a transparent portion by perforation with a hole or multiple holes, so that the photodetector can detect the excitation radiation in the above-described manner.

In the case of a fundus camera as shown in FIG. 2, the calibration device of FIG. 9 can also emulate further characteristics of the object under investigation, e.g. can be modeled like an eye, so that also the optical path in the eye can be taken into account in the calibration.

In accordance with requirements of the specific application, the embodiments of the invention as described above and individual features thereof can be modified and combined with each other by a skilled person. For example, microscope-like arrangements which deviate from the above-mentioned examples can be employed. Further, the used optical elements can be adapted according to the requirements. Also, instead of conventional LEDs and laser diodes also VCSELs (Vertical Cavity Surface Emitting Lasers), VECSELs (Vertical External Cavity Surface Emitting Lasers) or SLDs (Super Luminescence Diodes) can be used as semiconductor-based radiation sources.

The invention claimed is:

1. A device for measuring luminescence, comprising:
an electronic pulse generator for generating a periodic modulation signal having rectangular pulses, a pulse duration of the pulses being variably adjustable,
illumination means for illuminating an object under investigation with excitation radiation, the illumination means being controlled by the modulation signal to modulate the excitation radiation in a pulse-like manner depending on the modulation signal, and
a time-of-flight camera for phase-sensitive detection of a luminescence response emitted by the object under investigation in response to the excitation radiation, the modulation signal being provided as a reference signal to the time-of-flight camera.

2. A method of measuring luminescence, comprising:
generating a periodic modulation signal having rectangular pulses,
generating excitation radiation modulated in a pulse-like manner depending on the modulation signal,
illuminating an object under investigation with the excitation radiation,
providing the modulation signal as a reference signal to a time-of-flight camera, and
performing phase-sensitive detection with the time-of-flight camera of a luminescence response emitted by the object under investigation in response to the excitation radiation for different pulse durations.

3. The method according to claim 2, comprising:
calculating a luminescence lifetime of at least one material contained in the object under investigation depending on a signal strength of the luminescence response detected by the time-of-flight camera for a plurality of pulse durations of the modulation signal.

4. The method according to claim 3, comprising:
calculating the luminescence lifetime depending on a phase position of the luminescence response detected by the time-of-flight camera.

5. The method according to claim 3, comprising:
calculating the luminescence lifetime on the basis of a normalized modulation depth of the luminescence response determined for different pulse durations.

6. The method according to claim 2, comprising:
calculating the respective luminescence lifetime of a least two materials contained in the object under investigation.

7. The method according to claim 2, wherein one of the pulse durations, for which the luminescence response is detected, is selected to be significantly larger than a maximum expected luminescence lifetime.

8. The method according to claim 2, comprising:
introducing a semiconductor-based radiation source and a photodetector into an optical path of the excitation radiation and of the luminescence response;
detecting a pulse of the excitation radiation with the photodetector;
controlling the semiconductor-based radiation source to emit a pulse-shaped response radiation after a predetermined delay time after detecting the pulse of the excitation radiation;
detecting the response radiation with the time-of-flight camera; and
calibrating a run-time detected by the time-of-flight camera on the basis of the predetermined delay time.

9. A device for measuring luminescence, comprising:
an electronic pulse generator operable to generate a periodic modulation signal having rectangular pulses with a pulse duration and to variably adjust the pulse duration of the rectangular pulses;
an illumination device operable to illuminate an object under investigation with excitation radiation, the illumination device being connected to the electronic pulse generator and being controlled by the periodic modulation signal to modulate the excitation radiation in a pulse-like manner dependent upon the periodic modulation signal; and
a time-of-flight camera operable to perform phase-sensitive detection of a luminescence response emitted by the object under investigation in response to the excitation radiation, the time-of-flight camera being connected to the electronic pulse generator and receiving the periodic modulation signal from the electronic pulse generator as a reference signal.

10. The device according to claim 9, wherein the illumination device is operable to illuminate the object under investigation in a line-like manner.

11. The device according to claim 10, wherein the time-of-flight camera comprises a plurality of detector elements disposed in a line.

12. The device according to claim 9, wherein the illumination device is operable to illuminate the object under investigation in a two-dimensional manner.

13. The device according to claim 12, wherein the time-of-flight camera comprises a plurality of detector elements disposed in a grid.

14. The device according to claim 9, further comprising an objective having an objective plane and being operable to detect the luminescence response, the illumination device being operable to illuminate the object under investigation with a light blade having a light blade plane substantially perpendicular to the objective plane.

15. The device according to claim 9, wherein the luminescence response has a signal strength and the time-of-flight camera is operable to determine the signal strength; and
further comprising an evaluation device operable to calculate a luminescence lifetime of at least one material contained in the object under investigation dependent upon the signal strength of the luminescence response determined by the time-of-flight camera for a plurality of pulse durations of the periodic modulation signal.

16. The device according to claim 15, wherein:
the luminescence response has a phase position;
the time-of-flight camera is operable to detect the phase position of the luminescence response; and
the evaluation device is operable to calculate the luminescence lifetime dependent upon the phase position of the luminescence response detected by the time-of-flight camera.

17. The device according to claim 15, wherein the evaluation device is operable to determine the luminescence lifetime based upon a normalized modulation depth determined for different pulse durations.

18. The device according to claim 9, wherein the illumination device comprises at least one semiconductor-based radiation source.

19. The device according to claim 18, wherein the at least one semiconductor-based radiation source comprises a current driver operable to generate an operating current dependent upon the periodic modulation signal.

20. The device according to claim 9, wherein the illumination device comprises a plurality of semiconductor-based radiation sources, and further comprising a couple operable to couple the respective output radiation of the semiconductor-based radiation sources into a single optical path.

21. The device according to claim 20, wherein the couple comprises at least one of:
a plurality of color splitters; and
a rotational mirror.

22. The device according to claim 9, wherein at least one of the electronic pulse generator, the illumination device, and the time-of-flight camera defines at least one common optical path for the excitation radiation and the luminescence response.

23. The device according to claim 9, further comprising a radiation homogenizer associated with the excitation radiation and operable to homogenize the excitation radiation.

24. The device according to claim 9, further comprising at least one multi-band filter operable to filter at least one of the excitation radiation and the luminescence response.

25. The device according to claim 9, wherein the excitation radiation has an optical path, the luminescence response has an optical path, and further comprising a calibration device operable to be selectively introduced into the optical path of at least one of the excitation radiation and the luminescence response instead of the object under investigation and to generate a response radiation having a predetermined phase shift.

26. The device according to claim 25, wherein:
the calibration device comprises a semiconductor-based radiation source and a photodetector; and
the semiconductor-based radiation source is controlled to generate a pulse of the response radiation a predetermined time after detecting a pulse of the excitation radiation through the photodetector.

27. The device according to claim 25, wherein the calibration device is operable to variably adjust the predetermined phase shift of the response radiation.

28. The device according to claim 9, wherein the periodic modulation signal has a frequency of at least 1 MHz.

* * * * *